(12) United States Patent
Quackenbush et al.

(10) Patent No.: US 12,005,166 B2
(45) Date of Patent: Jun. 11, 2024

(54) BREAST PUMP

(71) Applicant: Momtech, Inc., Matthews, NC (US)

(72) Inventors: Carr Lane Quackenbush, Monson, MA (US); Scott Liddle, Raleigh, NC (US); Scott Cooper, Apex, NC (US); Erin Simons, Raleigh, NC (US)

(73) Assignee: Momtech Inc., Matthews, NC (US)

( * ) Notice: Subject to any disclaimer, the term of this patent is extended or adjusted under 35 U.S.C. 154(b) by 0 days.

(21) Appl. No.: 17/819,481

(22) Filed: Aug. 12, 2022

(65) Prior Publication Data

US 2022/0378989 A1 Dec. 1, 2022

Related U.S. Application Data

(60) Continuation-in-part of application No. 17/473,838, filed on Sep. 13, 2021, now Pat. No. 11,413,381.
(Continued)

(51) Int. Cl.
*A61M 1/06* (2006.01)
*A61M 39/24* (2006.01)

(52) U.S. Cl.
CPC ............ *A61M 1/064* (2014.02); *A61M 39/24* (2013.01); *A61M 2205/3344* (2013.01)

(58) Field of Classification Search
CPC ........ A61M 1/06; A61M 1/062; A61M 1/064; A61M 1/066; A61M 1/75; A61J 13/00; A61J 9/00; A61J 9/001
See application file for complete search history.

(56) References Cited

U.S. PATENT DOCUMENTS

| | | | |
|---|---|---|---|
| 2,864,628 A | | 12/1958 | Edleson |
| 4,263,912 A | * | 4/1981 | Adams .................. A61M 1/064 |
| | | | 604/75 |

(Continued)

FOREIGN PATENT DOCUMENTS

| | | |
|---|---|---|
| CA | 2240268 A1 | 12/1999 |
| CN | 107616921 A | 1/2018 |

(Continued)

OTHER PUBLICATIONS

PCT Application No. PCT/US2017/68633, ISR and Written Opinion dated Mar. 19, 2018.
(Continued)

*Primary Examiner* — Scott J Medway
(74) *Attorney, Agent, or Firm* — Lathrop GPM LLP; Wm. Tucker Griffith

(57) ABSTRACT

A breast pump device and associated methods for extracting breast milk are disclosed. A pump head comprises an external shell with an elastic membrane disposed and bonded therein to define at least one hermetically sealed chamber. Manipulation of the elastic membrane, for example, by adjusting suction or pressure in the sealed chamber or within an interior volume defined by the elastic membrane permits radial mechanical compression (positive pressure) to be applied to a nipple positioned in the pump head to simulate compression of the nipple by the infant's tongue and simultaneously permits axial hydraulic or pneumatic suction (negative pressure) to be applied to the nipple to simulate the infant's minimum intra-oral vacuum. The breast pump device of the present invention can generate these simultaneous compressions and suctions with a single vacuum source, which may be an electric pump or a hand-operated mechanical pump.

20 Claims, 5 Drawing Sheets

Related U.S. Application Data which is a continuation-in-part of application No. 17/060,302, filed on Oct. 1, 2020, now Pat. No. 11,147,905, and a continuation-in-part of application No. 17/036,605, filed on Sep. 29, 2020, now Pat. No. 11,116,880, said application No. 17/060,302 is a continuation-in-part of application No. 16/251,198, filed on Jan. 18, 2019, now Pat. No. 10,806,837, which is a continuation-in-part of application No. 16/004,742, filed on Jun. 11, 2018, now Pat. No. 10,286,130, which is a division of application No. 15/403,578, filed on Jan. 11, 2017, now Pat. No. 10,016,548.

(60) Provisional application No. 62/927,365, filed on Oct. 29, 2019.

(56) References Cited

U.S. PATENT DOCUMENTS

| | | | |
|---|---|---|---|
| 4,607,596 A | | 8/1986 | Whittlestone et al. |
| 4,857,051 A | | 8/1989 | Larsson |
| 4,883,464 A | * | 11/1989 | Morifuki ............ A61M 1/064 604/74 |
| 5,749,850 A | * | 5/1998 | Williams ............ A61M 1/06 604/320 |
| 5,941,847 A | * | 8/1999 | Huber ............ A61M 1/066 604/74 |
| 6,090,065 A | * | 7/2000 | Giles ............ A61M 1/062 604/74 |
| 6,273,868 B1 | | 8/2001 | Nordvik |
| 6,673,036 B1 | | 1/2004 | Britto |
| 6,749,582 B2 | | 6/2004 | Britto et al. |
| 6,840,918 B1 | * | 1/2005 | Britto ............ A61M 1/06935 604/74 |
| 6,887,210 B2 | | 5/2005 | Quay |
| 7,101,350 B2 | | 9/2006 | Ytteborg |
| 7,875,000 B2 | | 1/2011 | Krebs et al. |
| 7,988,661 B2 | | 8/2011 | Silver et al. |
| 8,052,635 B1 | | 11/2011 | Kelly |
| 8,118,772 B2 | | 2/2012 | Dao et al. |
| 8,187,219 B1 | * | 5/2012 | Chiang ............ A61H 9/0057 604/74 |
| 8,216,179 B2 | | 7/2012 | Bosshard et al. |
| 8,961,454 B2 | | 2/2015 | Chen |
| 10,016,548 B1 | | 7/2018 | Quackenbush |
| 10,286,130 B2 | | 5/2019 | Quackenbush |
| 10,485,908 B2 | | 11/2019 | Mvarez |
| 10,806,837 B2 | | 10/2020 | Quackenbush |
| 11,116,880 B2 | | 9/2021 | Quackenbush |
| 11,147,905 B2 | | 10/2021 | Quackenbush |
| 2002/0198489 A1 | * | 12/2002 | Silver ............ A61M 1/064 119/14.47 |
| 2004/0158199 A1 | | 8/2004 | McKendry et al. |
| 2004/0182813 A1 | | 9/2004 | Gilmore |
| 2004/0249340 A1 | * | 12/2004 | Britto ............ A61M 1/06 604/74 |
| 2005/0154349 A1 | * | 7/2005 | Renz ............ A61M 1/0697 604/74 |
| 2005/0234370 A1 | | 10/2005 | Kobayashi |
| 2006/0106334 A1 | | 5/2006 | Jordan |
| 2007/0060873 A1 | * | 3/2007 | Hiraoka ............ A61M 1/066 604/74 |
| 2009/0062731 A1 | * | 3/2009 | Keyong ............ A61M 1/06 604/74 |
| 2014/0121593 A1 | | 5/2014 | Felber et al. |
| 2014/0288466 A1 | | 9/2014 | Alvarez et al. |
| 2014/0378946 A1 | | 12/2014 | Thompson |
| 2015/0065994 A1 | | 3/2015 | Fridman et al. |
| 2016/0000982 A1 | | 1/2016 | Alvarez et al. |
| 2016/0206794 A1 | | 7/2016 | Makower et al. |
| 2016/0058928 A1 | | 9/2016 | Nowroozi et al. |
| 2017/0312409 A1 | | 11/2017 | Alvarez |
| 2018/0021222 A1 | | 1/2018 | Quackenbush |
| 2018/0093024 A1 | * | 4/2018 | Analytis ............ A61M 1/062 |
| 2019/0240386 A1 | | 8/2019 | Larsson |

FOREIGN PATENT DOCUMENTS

| | | |
|---|---|---|
| CN | 2011024183 U | 7/2020 |
| JP | 2011510765 A | 4/2011 |
| WO | 2004058330 A1 | 7/2004 |

OTHER PUBLICATIONS

N.P.Aleekseev, E.V. Omel'yanyuk, and N.E. Talalaeva, Dynamics of Milk Ejection Reflexes Accompanying Continuous 2 Rhythmic Stimulation of the Areola-Nipple Complex of the Mammary Gland, 2000, Ros. Fiziol, Zhum, im. I.M. Sechenova, vol. 86, No. 6, pp. 711-719 (Year: 2000).

PCT/US2021.956848, International Search Report and Written Opinion, dated Feb. 15, 2022.

* cited by examiner

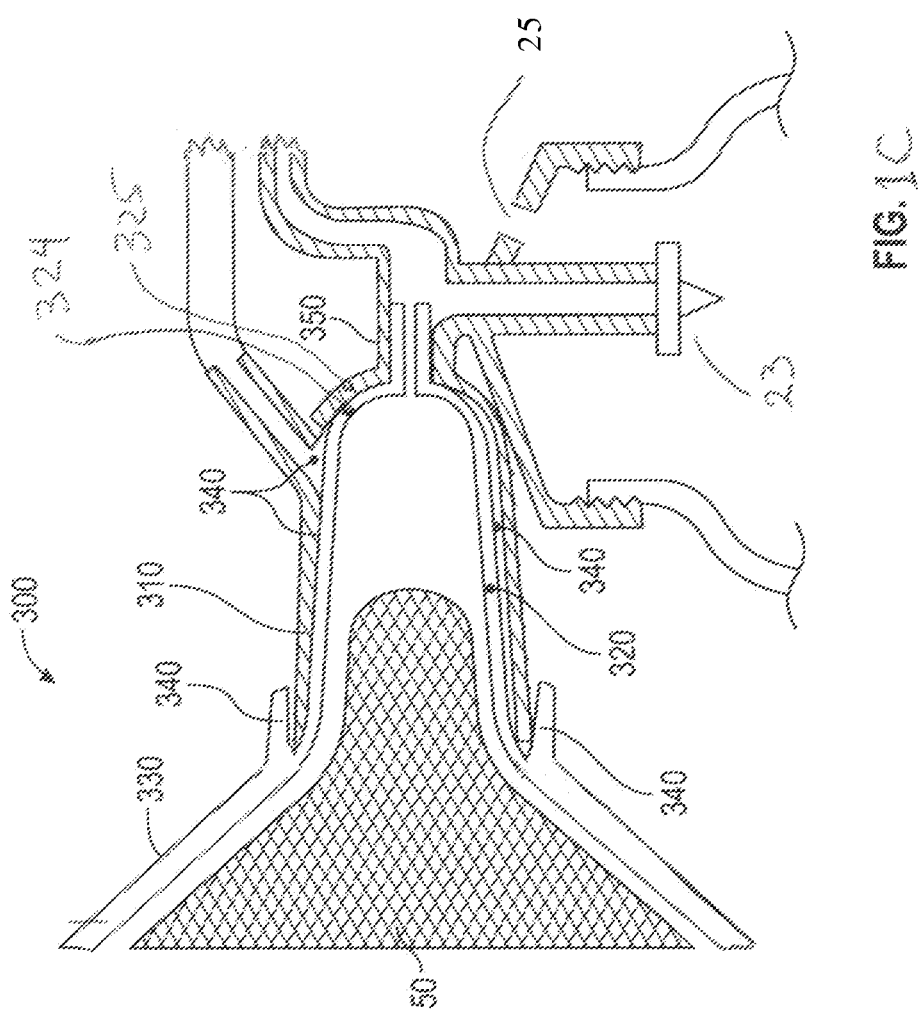

BREAST PUMP

CROSS-REFERENCE TO RELATED APPLICATIONS

This application is a continuation-in-part of U.S. patent application Ser. No. 17/473,838, filed Sep. 13, 2021, issued as U.S. Pat. No. 11,413,381, which is a continuation-in-part application of U.S. patent application Ser. No. 17/060,302, filed Oct. 1, 2020, which is a continuation-in-part of U.S. patent application Ser. No. 16/251,198, filed Jan. 18, 2019, issued as U.S. Pat. No. 10,806,837, which is a continuation of U.S. patent application Ser. No. 16/004,742, filed Jun. 11, 2018, issued as U.S. Pat. No. 10,286,130, which is a divisional of U.S. patent application Ser. No. 15/403,578, filed Jan. 11, 2017, issued as U.S. Pat. No. 10,016,548, each of which is hereby incorporated by reference in its entirety.

U.S. patent application Ser. No. 17/473,838 is also a continuation-in-part of U.S. patent application Ser. No. 17/036,605, filed Sep. 29, 2020, which claims the benefit of U.S. Provisional Application No. 62/927,365, Filed Oct. 29, 2019, each of which is hereby incorporated by reference in its entirety.

TECHNICAL FIELD OF THE INVENTION

The present invention relates generally to milking and breast pump devices and, more particularly, to breast pumps for lactating females designed to mimic the natural suckling action of an infant during breast-feeding. The present invention has applicability to electric breast pumps and manual breast pumps alike. The present invention also relates to a method of extracting breast milk using such a breast pump device as described and illustrated herein.

BACKGROUND OF THE INVENTION

Newborns and infants experience immediate and long-term benefits from breast milk feeding that are well documented. (See Cunningham A. S., Jelliffe D. B., Jelliffe E. F., *Breast feeding and health in the 1980s: a global epidemiological review, Journal of Pediatrics*, 1991, 118:659-666). These benefits include providing protection against many illnesses caused by allergies, bacteria and viruses, such as stomach viruses, respiratory illnesses, ear infections, meningitis and the like. (See Fallot M. E., Boyd J. L., Oski F. A., *Breast-feeding reduces incidence of hospital admissions for infection in infants, Pediatrics*, 1980, 65:1121-1124). Breast milk feeding also may increase intelligence and fight obesity.

Nursing mothers may desire to impart the above-noted benefits of breast milk to their infant when the two are separated. Additionally, traditional nursing may not be possible, or convenient, at all times and locations. Thus, to extract breast milk to later feed to the infant, nursing mothers can use a breast pump. The extracted breast milk can be fed to the infant using a bottle fitted with an artificial teat.

Nature is the design gold standard. Ideally, a breast pump should replicate the action of a nursing infant. So, it is instructive to review research on mother/infant nursing versus the action of various commercial breast pumps and milking machines.

Milk Ejection Reflex (MER) and Breast Pressurization

It is generally accepted that significant milk can be expressed only if there is an adequate milk ejection reflex (MER) and to remove milk in large quantities normally requires an MER, nipple extension and application of vacuum by the infant. Research indicates mechanical stimulation of the areola, presumably by the infant's gums and tongue brings on repeated MERs. (See N. P. Alekseev, E. V. Omel'yanyuk, et al. (2000) "*Dynamics of milk ejection reflex during continuous rhythmic stimulation of areola-nipple complex of the mammary gland,*" Rossiiskii Fiziologicheskii Zhurnal Imeni I. M. Sechenova, 86(6):711-719). However, stimulation of the nipple or the breast proximal to the areola does not cause an MER.

MER initiation is a multi-step sequence. Mechanical stimulation of the areola causes a nerve impulse to the hypothalamus, which causes oxytocin to be released from the pituitary gland into the bloodstream. Oxytocin causes contraction of the starfish-like myoepithelial cells surrounding the alveoli (milk producing sacks) in the breast causing intra-ductal pressure to increase, squeezing the milk forward toward the nipple tip.

Direct measurement shows this pressure to be about 20 ml Hg (Cobo, E., M. M. De Bernal, et al. (1967), "Neurohypophyseal *hormone release in the human, II. Experimental study during lactation,*" American Journal of Obstetrics and Gynecology, 97: 519-529). Further evidence of ductal pressure increase following an MER comes from ultrasound images showing the areolar ducts expanding from 1.6 mm before the MER to 2.8 mm after the MER. (See D. T. Ramsay, J. C. Kent, R. A. Owens and P. E. Hartmann, *Ultrasound Imaging of Milk Ejection in the Breast of Lactating Women, Pediatrics*, 2004; 113:361).

Thus, a requirement for milk extraction is that the highly elastic nipple ducts must be expanded by internal pressure from an MER. Without duct expansion, suction will collapse the highly elastic nipple ducts, blocking milk transmission.

Oxytocin has a half-life of less than 4 minutes, a very short time. (See G. Rydén and I. Sjöholm, *Half-life of oxytocin in blood of pregnant and non-pregnant women, European Journal of Endocrinology*, 1969, Vol 61: Issue 3; pg. 425-431). This means the MER pressure event lasts only a few minutes. If an infant wants more milk, it must create a new MER to repressurize the system. Oxytocin's short half-life thus creates a pressure control mechanism.

Nipple Structure, Valves within the Nipple

Ultrasonic imaging and the typical behavior of a nursing breast/nipple give evidence for two normally closed valves within the nipple.

The first, located within the nipple, opens when the nipple is elongated. Evidence for this valve are ultrasonic images showing that after an MER, nipple ducts of the non-nursed nipple are barely visible whereas on the nursing side, with the nipple elongated, the nipple ducts are expanded. Further evidence is the observation that after an MER both breasts are pressurized but the non-nursing breast does not spray, presumably because that nipple is not elongated.

The other valve is a sphincter near the nipple tip. It opens if there is sufficient suction to pull milk through it. Warmth can also relax and open it—e.g., the warmth of the infant's mouth or when warm wet towels are used to extract milk in Japanese hand massage.

In nursing, the infant elongates the nipple until the nipple is seated into the downward curve of the hard palate at the back of the infant's mouth. It is reported that this elongation can be two times the rest length of the nipple. (See Smith, W. L., Erenberg, A. and Nowak, A. J. (1988), *Imaging Evaluation of the Human Nipple During Breastfeeding, Am J Diseases in Children*, 142:76-78).

Mechanical Nursing Action by the Infant

After the nipple is extended and an MER is achieved, the nursing cycle begins: The cycle generally comprises the following steps:

1. First, the infant drops its tongue. This increases volume in the back of the mouth. This increases suction and, because the nipple is already fully extended and seated, this volume increase cannot be filled by any further increase of nipple length. Milk flows to fill the increased volume.
2. When sufficient milk has been extracted. The infant stops tongue lowering, then reverses the tongue motion. Maximum suction occurs at the bottom of the stroke and decreases as the tongue moves up.
3. When the tongue is fully up, ultrasound evidence shows that the infant compresses the nipple against the roof of its mouth, squeezing the milk ducts closed which stops flow. (See McClellan, H. L., Sakalidis, V. S., Hepworth, P. R., Hartmann, P. E. and Geddes, D. T. (2010), *Validation of Nipple Diameter and Tongue Movement Measurements with B-Mode Ultrasound During Breastfeeding, Ultrasound in Medicine & Biology,* 36 (11):1797-1807). Swallowing ensues.

In the nursing cycle, the infant compresses the nipple to stop flow so it can swallow without flooding. Nipple compression has an unintended benefit for the mom, it prevents pooling/accumulation of liquid in the nipple tissue. This painful condition, generally caused when tissue has prolonged exposure to vacuum, is known as edema.

Suction Cycle of the Nursing Infant

Intra-oral vacuum traces measured with a pressure probe in a nursing infant's mouth shows vacuum up to about −180 mm Hg. (D. T. Geddes et. al. (2008), *Tongue movement and intra-oral vacuum in breastfeeding infants, Early Human Development,* 84, 471-477). Ultrasound video studies show milk flowing only during the maximum suction portion of the curve.

An Ideal Breast Pump

All current commercial breast pumps, including both manual and electric breast pumps, use vacuum (i.e., negative air pressure) applied to the mother's breast to extract milk. Conventional breast pumps using only vacuum can cause significant pain to the mother, or even edema in nursing mothers, which inhibits the collection and even production of breast milk.

Therefore, it is desirous to provide an improved approach to breast pumps, and operation thereof, that more closely mimic the natural suckling action of the infant and does not cause pain or edema.

A breast pump which mimics the natural nursing cycle must be able to duplicate the mechanical action and suction cycles of the nursing infant. This requires mechanisms which can:

1. Bring on an MER to pressurize the breast;
2. Extend the nipple to enable milk flow;
3. Create suction of about 180 mm Hg to extract milk; and
4. Apply radial (mechanical) compression to the nipple to control nipple edema—this radial (mechanical) compression must be applied when axial (milk extraction) suction is at its lowest level.

A pump capable of applying positive pressure for nipple compression is a significant design challenge addressed by the present invention.

DESCRIPTION OF THE RELATED ART

Commercial breast pumps use cyclic vacuum (negative air pressure) applied to the mother's nipple, typically inside a hard, plastic shell, to extract milk. In comparing the required mechanisms for a breast pump, listed above, for mimicking the natural nursing cycle, conventional pumps exhibit the following limitations or drawbacks:

1. All breast pumps can generally bring on an MER to pressurize the breast. Many pumps have a "stimulation phase." For example, pump promotional information claims a 120 cycle/minute stimulation cycle creates the MER. However, this is an inadequate explanation, as early pumps having only an extraction cycle as low as 40 cycles/min and no stimulation phase are still able to create an MER. A more plausible explanation is that the cyclic vacuum which causes the nipple to elongate and retract by a factor of 2 times, is repeatedly dragging the areola across the inflection between the breast shield funnel and nipple tunnel causing a mechanical stimulation of the areola.
2. All breast pumps can extend the nipple and extract milk
3. All breast pumps can create suction of about 180 mm Hg to extract milk.
4. None of the conventional breast pumps can apply radial (mechanical) compression to the nipple. This is a major shortcoming of commercial pumps leading to nipple edema which can cause nipples to swell until they completely fill the nipple tunnel, a painful condition. In the natural nursing cycle, nipple compression occurs when the infant's tongue compresses the nipple against the roof of the mouth. This compression squeezes the milk ducts closed, stopping flow so the infant can swallow without gaging. Nipple compression also prevents edema in the mom's nipple.

SUMMARY OF THE INVENTION

The present invention provides a breast pump and a method for using said breast pump for extracting breast milk from a breast that more closely mirrors the natural suckling action of an infant, including nipple compression. As a result, the present invention improves upon the extraction and collection of breast milk generally associated with breast pumps.

The breast pump device in accordance with the present invention generally comprises an expandable and contractable elastic membrane adapted to surround the nipple. One embodiment of the present breast pump is a device capable of applying radial mechanical compression (positive pressure) to replicate compression of the nipple by the infant's tongue and is also capable of applying hydraulic or pneumatic suction (negative pressure) to extend the nipple and to extract milk. Additionally, the elasticity, expansion and contraction capability of the elastic membrane enables the device to fit a wider range of nipple diameters than conventional breast pumps having nipple tunnels made strictly of hard plastic.

According to embodiments of the present invention, a device for extracting breastmilk from a breast, such as a breast pump, comprises an external shell defining an internal cavity and an elastic membrane disposed in said internal cavity. The external shell includes a neck portion defining a proximal end and a distal end, and a feed channel defined at the distal end of the neck portion. The internal cavity of the external shell is in operative communication with at least one of a suction source and a positive pressure source via at least one opening in the external shell. The elastic membrane includes a funnel-shaped portion configured to receive and seal against the breast of a user, and a neck portion extending from the funnel-shaped portion and defining a proximal end and a distal end adapted to receive and position a nipple of the breast and narrowing at the distal end to an exit port. The neck portion of the elastic membrane generally fits in the neck portion of the external shell such that the exit port of the elastic membrane is in operative communication with the feed channel. The exterior of the elastic membrane is sealed to the interior of the external shell to form a hermetic chamber between the neck portion of the external shell and the neck portion of the elastic membrane. When the nipple of the user is positioned in the neck portion of the elastic membrane, an unoccupied volume is defined between the nipple tip and the distal end of the elastic membrane.

In accordance with embodiments of the present invention, a suction below atmospheric pressure is applied inside the elastic membrane around and in front of the nipple positioned therein, to extend the nipple towards the distal end of the neck portion of the elastic membrane and to extract breast milk. The neck portion of the elastic membrane is also configured to relax radially outwardly, allowing clearance for the nipple to extend when a suction is introduced inside the hermetic chamber, wherein such suction in the hermetic chamber is equivalent to the suction pressure applied inside the elastic membrane around and in front of the nipple positioned therein. Additionally, a portion of the elastic membrane of the hermetic chamber is configured to expand radially inwardly when a positive pressure greater than the suction pressure then present inside the elastic membrane around and in front of the nipple is introduced into the hermetic chamber causing the elastic membrane to contact and compress the nipple to control nipple edema. Still further, the neck portion of the elastic membrane is configured for both radial outward and radial inward movement with alternating application of the suction pressure and the positive pressure into the hermetic chamber.

In another embodiment of the present invention, the feed channel of the external shell at the distal end of the neck portion is fitted with a check valve to limit dead volume which must be evacuated by the pump when in cyclic milk extraction mode. The hermetic chamber in the neck portion defined between the external shell and the elastic membrane, may be in operative communication with a source of alternating positive and negative pressure via at least one opening in said external shell. Additionally, a source of suction may be applied within the elastic membrane around and in front of the nipple, causing the nipple to extend and to extract breast milk. Still further, the neck portion of the elastic membrane of the hermetic chamber is configured to expand radially inwardly when a positive pressure is introduced into the hermetic chamber to compress the nipple to control nipple edema.

In accordance with the present invention, the various chambers formed within the breast pump device may be inflated and deflated with atmospheric pressure or with different positive pressure or suction from, for example, positive displacement electric or manual pumps capable of exerting alternating positive and negative pressure.

In embodiments of the present invention, the elastic membrane used in the breast pump device is capable of cycling between expanded and contracted states at a rate of 100 to 140 cycles per minute, preferably 120 cycles per minute, during stimulation mode to create a milk ejection reflex, and cycling between expanded and contracted states at a rate of 40 to 80 cycles per minute, preferably 60 cycles per minute, during milk extraction.

These and other objects, features and advantages of the present invention will become apparent in light of the detailed description of embodiments thereof, and as illustrated in the accompanying drawings.

BRIEF DESCRIPTION OF THE DRAWINGS

FIG. 1C shows a cross-sectional view of a breast pump in accordance with an alternate embodiment of the present invention, including a flexible funnel and an alternate attachment/seal arrangement between the external shell and the flexible elastic membrane.

DETAILED DESCRIPTION OF PREFERRED EMBODIMENTS

The following descriptions of the figures will convey details of construction and operation of breast pumps in accordance with the present invention.

As described herein, the term "vacuum" is used to connote negative air pressure, i.e., air pressure below atmospheric, whereas "suction" is used to connote negative pressure, i.e., pressure below atmospheric, in air-filled or liquid-filled systems. The term "positive pressure" is used to connote fluid pressure, air or liquid, above atmospheric pressure. "Expandable", "inflate", "inflated", "inflating", or similar terms, are used to connote an increase in size caused by applying positive fluid pressure to a hermetic chamber, i.e., pumping fluid into the chamber. "Contractible", "deflate", "deflated", "deflating", or similar terms, are used to connote a decrease in size caused by applying negative fluid pressure to a hermetic chamber, i.e., removing fluid from the chamber.

Additionally, the terms "proximal" and "distal" are used in their medical sense and directionally with respect to the user. Thus, the "distal portion" of the pump is farthest from the user. "Bottom", "lower" or "down" are generally used in reference to the orientation illustrated in the figures, which generally correspond to intended orientation of the device in use and signify a direction toward the milk collection container. Conversely, "top", "upper" or "up" refer to a direction away from the milk container.

The breast pump device in accordance with the present invention generally comprises an expandable and contractable elastic membrane adapted to surround the nipple and, in operation, mimics the natural suckling action of an infant during breast-feeding. The breast pump device as so designed and described hereinafter is capable of applying radial mechanical compression (positive pressure) to replicate compression of the nipple by the infant's tongue and is capable of applying hydraulic or pneumatic suction (negative pressure) to create and maintain nipple extension and replicate the infant's intra-oral vacuum for extraction of breast milk. More preferably, the present invention is directed to a breast pump device which can generate these compressions and suctions with a single pressure source, such as an electric pump or a hand-operated mechanical pump, which preferably can generate both positive pressure and suction within the breast pump device, as illustrated and described herein.

Figure 1A:
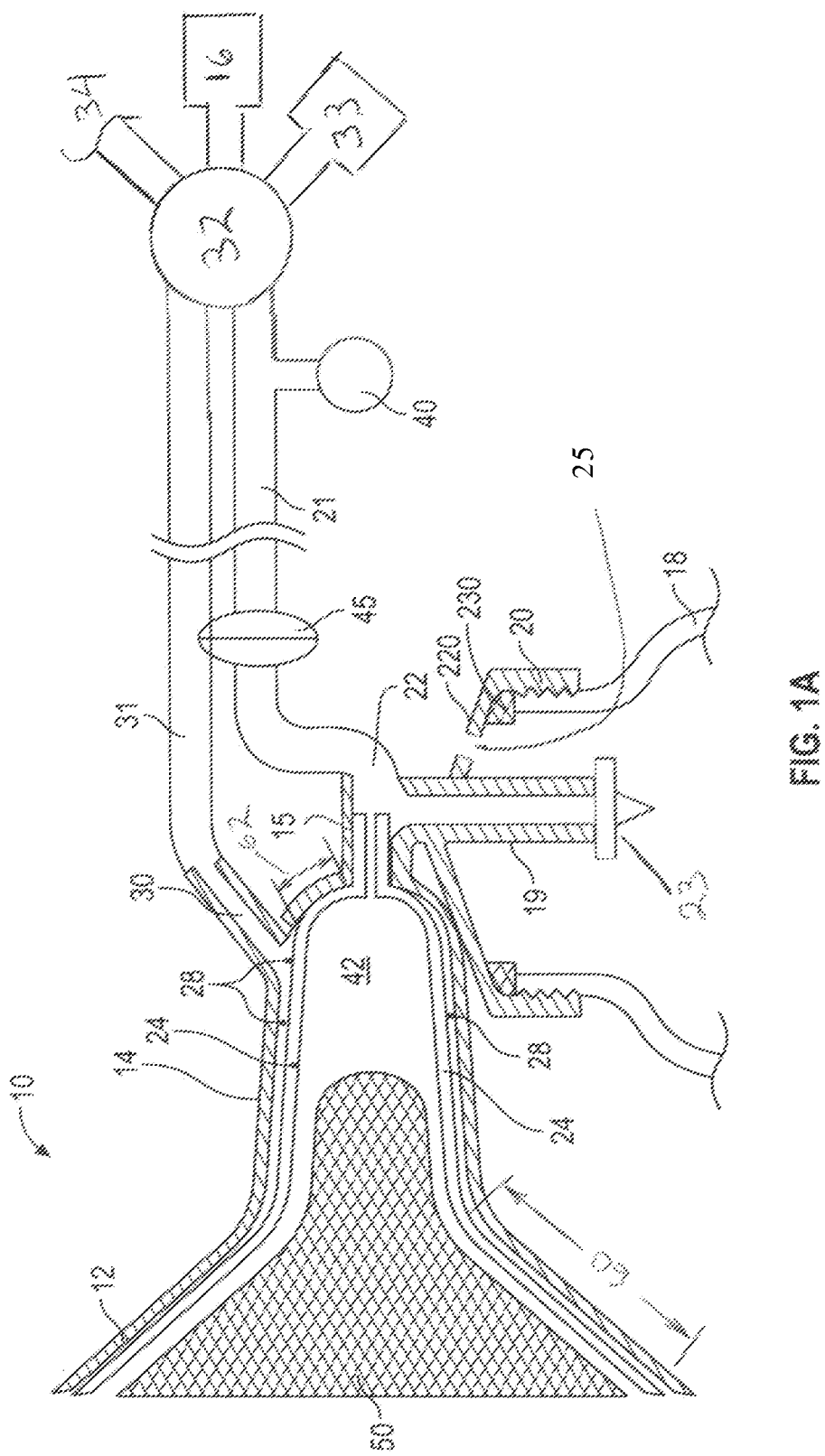
FIG. 1A shows a cross-sectional view of a breast pump in accordance with an embodiment of the present invention, including a 2-tube pump capable of continuous or cyclic vacuum to extend the nipple and extract milk and having an electric valve allowing atmospheric or positive pressure into the hermetic chamber to collapse an internal circumferential elastic membrane around the nipple to compress the nipple and thereby control edema.

Referring to FIG. 1A, an assembled breast pump for extracting breast milk in accordance with the present invention is generally designated as reference numeral 10. As shown, the assembled pumping head 10 includes an external hard shell comprising a funnel-shaped breast shield portion 12 adapted to press against a user's breast and which, as illustrated, narrows to a neck portion or nipple tunnel section 14 adapted to receive the nipple of a breast 50 therein, and an elastic or elastomeric membrane 24 is disposed inside the external hard shell. A feed channel 19 is located at the distal end 15 of the neck portion 14 and leads into a collection container 18, such as a bottle. Between the feed channel and the collection container is a check valve 23. The collection container 18 is connected to an attachment collar 220 of the pumping head 10 by threads 20 or other suitable connection means known in the art. A seal 230 can be formed between the collection container 18 and the attachment collar 220 to prevent leakage of collected breast milk. A hole 25 through the attachment collar maintains the interior of the collection container at atmospheric pressure and allows air to escape as milk fills the container.

Still referring to FIG. 1A, a port 22 at the distal end 15 of the neck portion 14 connects the interior 42 of the elastic membrane 24, through tubing 21, through an electric valve 32 which can connect tubing 21 to vacuum pump 16 or the electric valve 32 can close to isolate port 22 from the vacuum pump 16. A media separation device 45 may be disposed along tubing 21 between the port 22 at the distal end 15 of the neck portion 14 and the vacuum pump 16. The purpose of the media separation device 45 is to prevent milk collected in the breast pump 10 from entering the vacuum pump 16.

As noted, the elastic membrane 24 is disposed inside the external hard shell, and generally runs from within the proximal end of the funnel-shaped breast shield section 12 through the neck portion 14 and into the distal end 15 of the neck portion 14. Preferably, the exterior of the elastic membrane 24 is bonded to the interior of the of the external shell to form and maintain a hermetic chamber 28 between the external shell 12 and the elastic membrane 24. For example, as illustrated in FIG. 1A, the elastic membrane 24 is bonded to the inside surface of the funnel-shaped portion 12 of the external shell along region 60 and is also sealed to the inside surface of the distal end 15 of the neck portion 14 along region 62. Thus, hermetically sealed at both proximal and distal ends, the elastic membrane 24 forms a hermetic, toroidal, roughly tubular, chamber 28 located between the inside surface of at least the neck portion 14 of the external hard shell and the outside surface of a corresponding neck portion of the elastic membrane 24.

In preferred embodiments, the elastic membrane 24 is constructed of elastomeric materials selected from the group consisting of silicone rubber, thermoplastic elastomer (TPE), latex and the like.

A second port 30 through the external shell, leads out of the hermetic toroidal roughly tubular chamber 28 and connects to tubing 31 then to an electric valve 32 which can connect the chamber 28, through port 30 and tubing 31, to at least one of atmosphere (port 34) or a positive pressure source (port 33) or to the vacuum pump 16.

The space inside the elastic membrane 24 forms another chamber 42 which is contiguous with the feed channel 19 and with port 22 which leads to the electric valve 32 and to the vacuum pump 16. A pressure sensor 40 monitors output pressure of the pump 16, as well as the pressure in tubing 21 and in internal chamber 42.

Figure 2G:
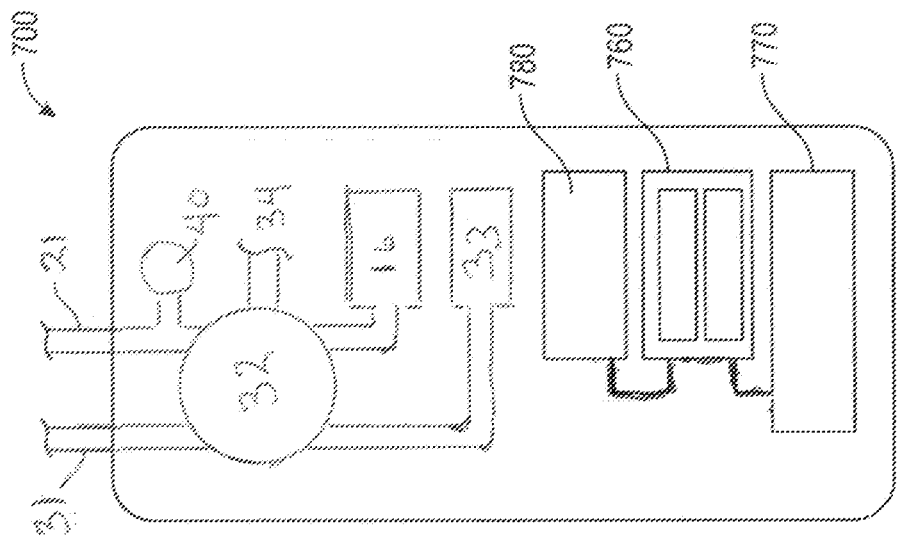
FIGS. 2A and 2B schematically illustrate the layout and internal components of the pump motor and control unit for electric pumps disclosed herein.

For the breast pump 10 of FIG. 1A, operating in cyclic vacuum MER mode, at start up, the control software and electronics 780 (as shown in FIG. 2B) start an MER sequence by switching valve 32, causing it to connect the interior 42 of the elastic membrane 24 and the hermetic chamber 28 to the vacuum pump 16. Device software then causes the vacuum pump to cycle between maximum vacuum and atmospheric pressure at about 100 to 140 cycles/minute, preferably 120 cycles/minute. Maximum MER vacuum can be user-selected or can be determined, for example, as a fraction of the user-selected maximum milk extraction vacuum used in the last pumping session. During this MER sequence, vacuum pressure on both sides of the neck portion of the elastic membrane 24 is always the same, so the elastic membrane 24 relaxes to its at-rest geometry which is away from the axis of the neck portion allowing the nipple to extend unimpeded when under suction. When suction is released, the nipple retracts somewhat. This cyclic elongation and retraction will repeatedly drag the areola across the inflection between the breast shield funnel portion 12 and neck portion 14 causing a mechanical stimulation of the areola. This is presumed to bring on an MER.

During startup, elongation of the nipple will displace air in front of the nipple in the chamber 42 within the elastic membrane 24, specifically in the interior volume between the nipple tip and the distal end of said elastic membrane 24. The displaced air is removed by the vacuum pump 16.

Figure 2A:
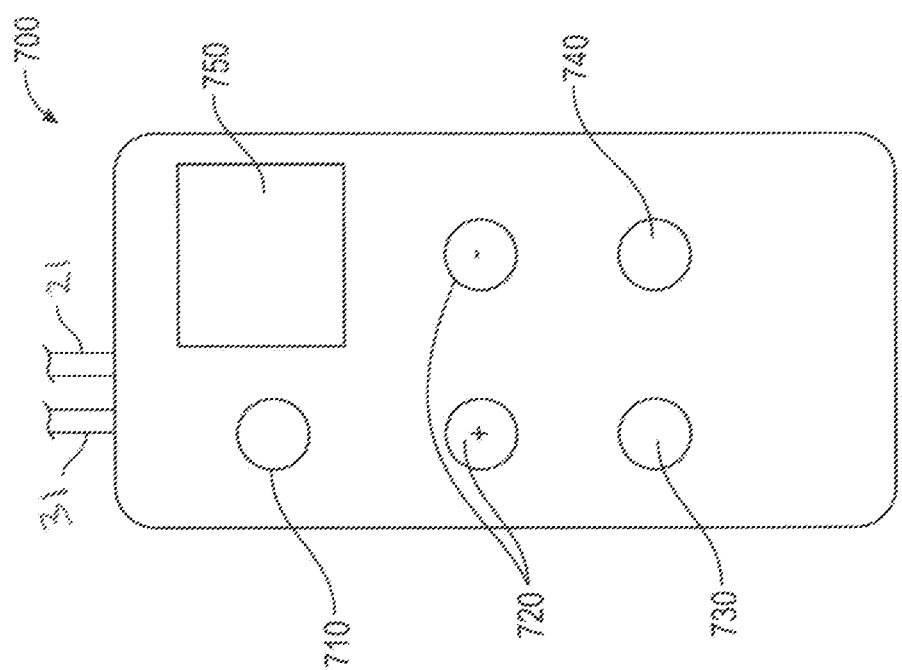

In preferred operation, the MER stimulation phase ends after expiration of a set time (e.g., two minutes) or by the user pressing the MER button 730 on the control panel generally illustrated in FIG. 2A. The MER button 730 comprises a toggle, which may be selected any time during the pumping session causing a change from MER stimulation cycle to milk extraction cycle or vice versa. After the end of the MER stimulation phase, the milk extraction cycle starts.

For the breast pump 10 of FIG. 1A, operating in cyclic vacuum milk extraction mode, the control software and electronics 780 (as shown in FIG. 2B) cause the electric valve 32 to connect the vacuum pump 16 to the interior 42 of the elastic membrane 24 and to the hermetic chamber 28. The user selects a maximum suction up to about −250 mm Hg using the +/− buttons 720 on the control panel (as shown in FIG. 2A). Device software then causes the vacuum pump 16 to cycle between maximum vacuum and atmospheric pressure at between 40 and 80 cycles/minute, preferably 60 cycles/minute. During the suction portion of the milk extraction sequence device software causes valve 32 to cycle so that vacuum pressure on both sides of the neck portion of the elastic membrane 24 is always the same, so the elastic membrane 24 relaxes to its at-rest geometry which is away from the axis of the neck portion allowing the nipple to extend unimpeded. Under suction from the vacuum pump 16, milk flows into feed channel 19, through the check valve 23 then into the collection container 18. During the cyclic vacuum milk extraction cycle, when suction falls to its lowest level, valve 32 switches allowing atmospheric (from port 34) or positive pressure (from positive pressure source 33) into tube 31 then into chamber 28 causing the neck portion of elastic membrane 24 to collapse radially inwardly around the nipple compressing it for the control of edema.

The breast pump 10 of FIG. 1A, may also be operated in constant vacuum milk extraction mode. In this, the control software and electronics 780 (as shown in FIG. 2B) cause the electric valve 32 to connect the vacuum pump 16 to the interior 42 of the elastic membrane 24 and to the hermetic chamber 28. The user selects a maximum suction up to about −250 mm Hg using the +/− buttons 720 on the control panel (as shown in FIG. 2A). Device software then causes the vacuum pump 16 to evacuate the interior 42 of the elastic membrane 24 and the hermetic chamber 28 to the maximum suction selected by the user. When the pressure monitor 40 determines that the maximum user-selected vacuum has been achieved it instructs the control software and electronics 780 to cause the electric valve 32 to close off connection to the interior 42 of the elastic membrane 24, sustaining the user-selected vacuum in that chamber. Next, the control software and electronics 780 causes the electric valve 32 to connect hermetic chamber 28 to a source of suction, providing vacuum up to the maximum user-selected level and alternately to atmosphere (via port 34) or a source of positive pressure (via port 33). The control software and electronics 780 cause the electric valve 32 to cycle the hermetic chamber 28 between maximum vacuum and atmospheric or positive pressure at between 40 and 80 cycles/minute, preferably 60 cycles/minute. Positive pressure (from positive pressure source 33) into tube 31 then into chamber 28 causes the neck portion of elastic membrane 24 to collapse radially inwardly around the nipple compressing it for the control of edema.

In constant vacuum milk extraction mode, pressure monitor 40 continuously compares vacuum in the collection container 18 and the interior 42 inside the elastic membrane 24 with the user-selected vacuum level. As needed system electronics will cause the electric valve 32 and vacuum pump 16 to eliminate any mismatch.

Figure 1B:
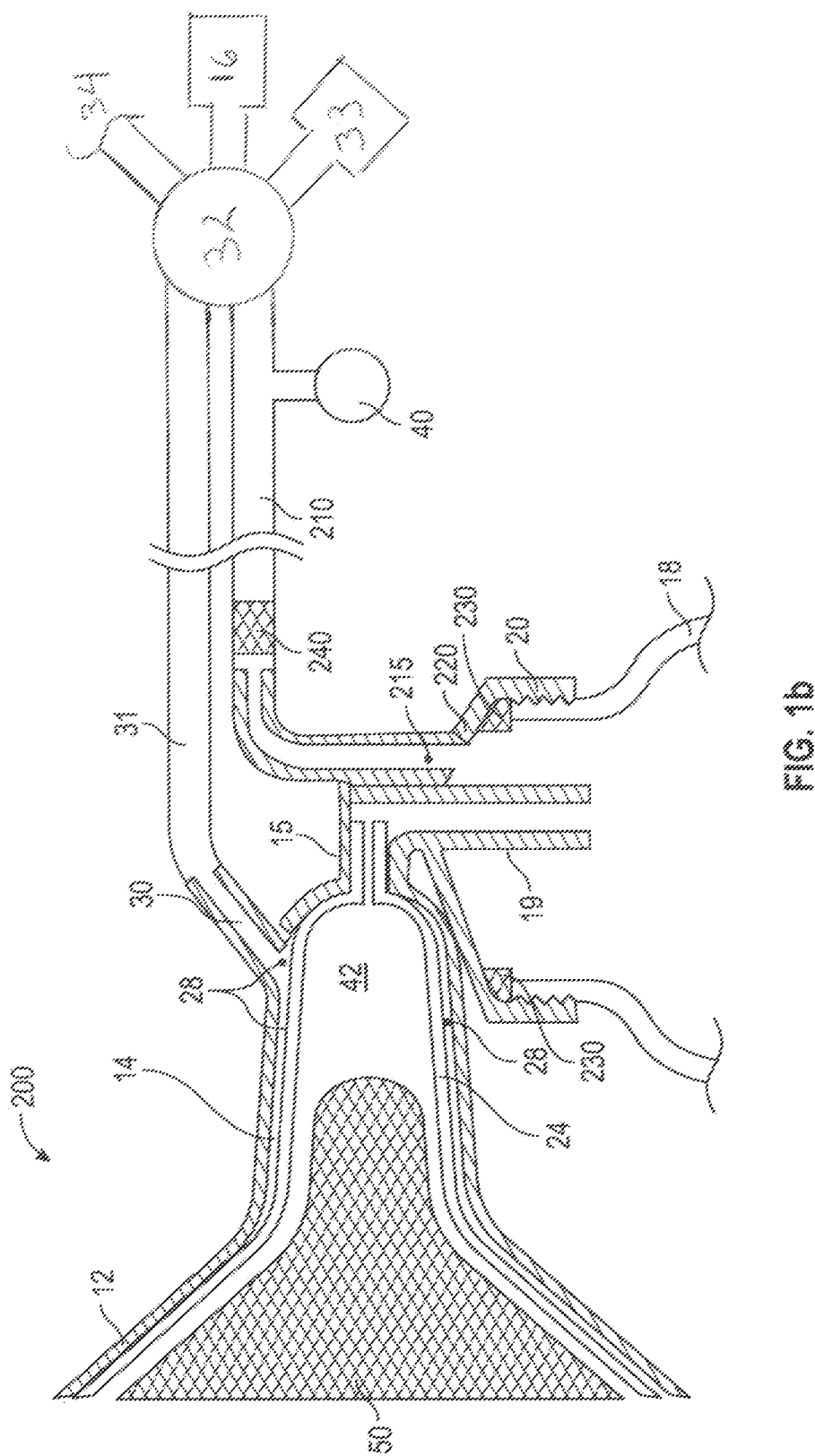
FIG. 1B shows a cross-sectional view of a breast pump in accordance with an alternate embodiment of the present invention, also including a 2-tube pump using continuous vacuum to extend the nipple and extract milk and having a valve allowing atmospheric pressure or positive pressure into the hermetic chamber to collapse an internal circumferential membrane around the nipple to compress the nipple and thereby control edema. The vacuum pump also is capable of evacuating a collection container eliminating need for a media separator.

Referring to FIG. 1B, an assembled breast pump for extracting breast milk in accordance with an alternate embodiment of the present invention is generally designated as reference numeral 200. The illustrated pumping head cross section 200 of FIG. 1B shares many features with pumping head 10 disclosed in FIG. 1A. Like components are designated by like reference numerals. In the embodiment of FIG. 1B, the vacuum pump 16 evacuates the collection container 18 to a constant vacuum so that the container 18 acts as a pressure reservoir and a pressure ballast to stabilize pressure fluctuations in chamber 42. To accommodate this change, the vacuum pump 16 is connected by electric valve 32 to tubing 210, to intake port 215, to the collection container 18 and to chamber 42, so all can be evacuated. In addition, the seal 230 is provided between the attachment collar 220 and the bottle 18 to make chamber 42, feed channel 19, the interior of the collection container 18 and the tubing 210 leading through electric valve 32 to the vacuum pump 16 into a single hermetic unit. In the configuration of FIG. 1B, breast milk from chamber 42 exits the feed channel 19 and falls into the collection container 18; this configuration gives significant physical separation between the milk stream, the milk surface in the collection container 18 and the intake port 215. This separation will help prevent aspiration of milk into tubing 210 and, moreover, from said tubing 210 into the vacuum pump 16. Decreased aspiration risk will likely eliminate the need for the media separator 45 illustrated in FIG. 1A, a significant design simplification. A simple in-line filter 240 may be needed to collect moisture from the warm breast milk and prevent it from condensing in tubing 210.

Breast pump 200 of FIG. 1B, only operates in constant vacuum milk extraction mode. At start up, the control software and electronics 780 start an MER sequence. First, the control software causes valve 32 to connect the vacuum pump 16 so it evacuates the hermetic chamber 28, the collection container 18, the feed channel 19 and the volume within the elastic membrane 24 (i.e., nipple chamber 42). Maximum MER vacuum can be user-selected or can be determined e.g., as a fraction of the user-selected maximum milk extraction vacuum used in the last pumping session. When the pressure monitor 40 determines that the maximum vacuum has been achieved it instructs the control software and electronics 780 to cause the electric valve 32 to close off connection to the collection container 18, the feed channel 19 and the interior 42 of the elastic membrane 24, sustaining vacuum in those chambers. Next, the control software and electronics 780 cause the electric valve 32 to connect hermetic chamber 28 alternately to the vacuum pump 16 and to either atmosphere (via port 34) or a source of positive pressure (via port 33). The control software and electronics 780 cause the electric valve 32 to cycle the hermetic chamber 28 between maximum vacuum and atmospheric or positive pressure at between about 100 to 140 cycles/minute, preferably 120 cycles/minute. As valve 32 cycles, the elastic membrane 24 relaxes radially outwardly—i.e., away from the axis of the breast pump 200—when suction is applied on both sides. The nipple elongates unimpeded under suction in chamber 42. When under atmospheric or positive pressure, elastic membrane 24 collapses around the nipple, mechanically compressing it and causing it to elastically retract somewhat. This cyclic elongation and retraction will repeatedly drag the areola across the inflection between the breast shield funnel portion 12 and neck portion 14 causing a mechanical stimulation of the areola. This is presumed to bring on an MER.

During startup, elongation of the nipple will displace air in front of the nipple in the chamber 42 within the elastic membrane 24, specifically in the interior volume between the nipple tip and the distal end of said elastic membrane 24. The displaced air is removed by the vacuum pump 16.

In preferred operation, the MER stimulation phase ends after expiration of a set time (e.g., two minutes) or by the user pressing the MER button 730 on the control panel. The MER button 730 comprises a toggle, which may be selected any time during the pumping session causing a change from MER stimulation cycle to milk extraction cycle or vice versa. After the end of the MER stimulation phase, the milk extraction cycle starts.

For breast pump 200 of FIG. 1B, operating in constant vacuum milk extraction mode, the user selects a maximum suction up to about −250 mm Hg using the +/− buttons 720 on the control panel. Device software causes valve 32 to connect the hermetic chamber 28, the collection container 18, the feed channel 19 and the interior of elastic membrane 24 (i.e., nipple chamber 42) and then causes vacuum pump 16 to evacuate these chambers. The suction level is monitored by pressure sensor 40 and is maintained constant by the system control electronics for the milk extraction session at the user-selected level. Periodically, at a cycle rate of between 40 and 80 cycles/minute, and preferably at a rate of 60 cycles/minute, the device software causes valve 32 to disconnect the hermetic chamber 28 from vacuum and connect it to either atmospheric pressure (via port 34) or a positive pressure source 33. With suction in the nipple chamber 42 and atmospheric pressure or (higher) positive pressure in the hermetic chamber 28, the neck portion of elastic membrane 24 will collapse radially inwardly around the nipple compressing it to control edema.

Referring to FIG. 1C, an assembled breast pump for extracting breast milk in accordance with an alternate embodiment of the present invention is generally designated as reference numeral 300. The illustrated pumping head cross section 300 of FIG. 1C shares many features as the pumping heads 10 and 200 disclosed in FIGS. 1A and 1B, respectively, and use common reference designations. In the embodiment of FIG. 1C, the funnel-shaped portion of the external shell (portion 12 illustrated in FIGS. 1A and 1B) is eliminated proximally from where it narrows to a nipple tunnel section 14. Instead, in the FIG. 1C configuration, the tubular elastic membrane 320 includes a proximal portion 330 that effectively forms a funnel-shaped portion for the breast shield. To form an attachment and seal between the external hard shell 310 of the neck portion, the tubular neck portion of the elastic membrane 320 and the funnel-shaped portion 330 of the elastic membrane/breast shield, a ring-shaped feature 340 is included on the tubular elastic membrane 320. This ring feature 340 extends distally from the outside surface of elastic membrane 320 and forms a hermetic seal with the proximal end of the external shell of the neck portion 310.

As in the embodiments of FIGS. 1A and 1B, the distal end of the elastic membrane 324 in FIG. 1C is sealed to the inside surface of the distal end 325 of the neck portion 310 of the external shell. Thus, sealed at both proximal and distal ends, the elastic membrane 320 of FIG. 1C forms a hermetic roughly tubular toroidal chamber 328 located between the inside surface of the neck portion 310 of the external shell and the outside surface of the neck portion of the elastic membrane 320.

The flexible elastic funnel-shaped portion of the FIG. 1C design improves user comfort over conventional hard plastic funnels.

The membrane seal design of FIG. 1C, utilizing the flexible funnel-shaped portion of the elastic membrane 330, can be applied to any pump embodiment disclosed in the present invention having a bonded distal end—e.g., the breast pumps 10 and 200 of FIGS. 1A and 1B respectively, without departing from the spirit and principles of the present invention.

A preferred design for the motor and control unit 700 used to drive any of the electric pump heads disclosed herein is generally illustrated in FIGS. 2A and 2B. As shown, the motor and control unit 700 has two tubes exiting as needed to drive a single breast shield. If the unit 700 is to power two breast shields, tubes 21 and 31 will each be split to drive the second breast shield.

The exterior of the motor and control unit 700 (FIG. 2A) has different buttons and a visual display. The buttons are, for example: on/off 710, milk extraction suction up/down buttons 720, MER toggle 730 and a display cycle button 740 that cycles the display 750 for example from extraction pressure to battery charge level to total pumping time. Other buttons or other display items may be added. The motor and control unit 700 may have internet connectivity to allow, for example, connection to cell phone or computer for control of pump operations, logging of data and/or connection to programs for analysis as may be desired by the user.

Internally, referring to FIG. 2B, valve 32 (using FIG. 1A as an example) can connect tube 31 or tube 21 either to the vacuum pump 16 or to atmosphere (via port 34) or a source of positive pressure 33. A pressure sensor 40 monitors output pressure of the pump; and when valve 32 connects them, it will also monitor pressure in tube 21.

In the embodiments of the present invention, the vacuum pump is powered by batteries 760 which are monitored and recharged by an AC charging system 770. Software and electronics 780 control the vacuum pump, pressure pump and valve according to pre-programmed logic, feedback from the pressure sensor 40 and user inputs.

The electrically powered pumps of FIG. 1A, 1B or 1C can be any of a number of positive displacement pumps: diaphragm, piston-driven, peristaltic or the like. The pumps can be configured to provide vacuum, positive pressure or both. The electric valve of these pumps can be a rotary valve, solenoid valve or other.

When the pumping session is complete, the on/off switch 72 on control panel is switched to the off position and a shutdown sequence is initiated. The valve 32 switches to vacuum so all elastic membranes are in their fully retracted position. Control electronics 780 then switch off the vacuum pump and the unit is fully off.

Figure 3:
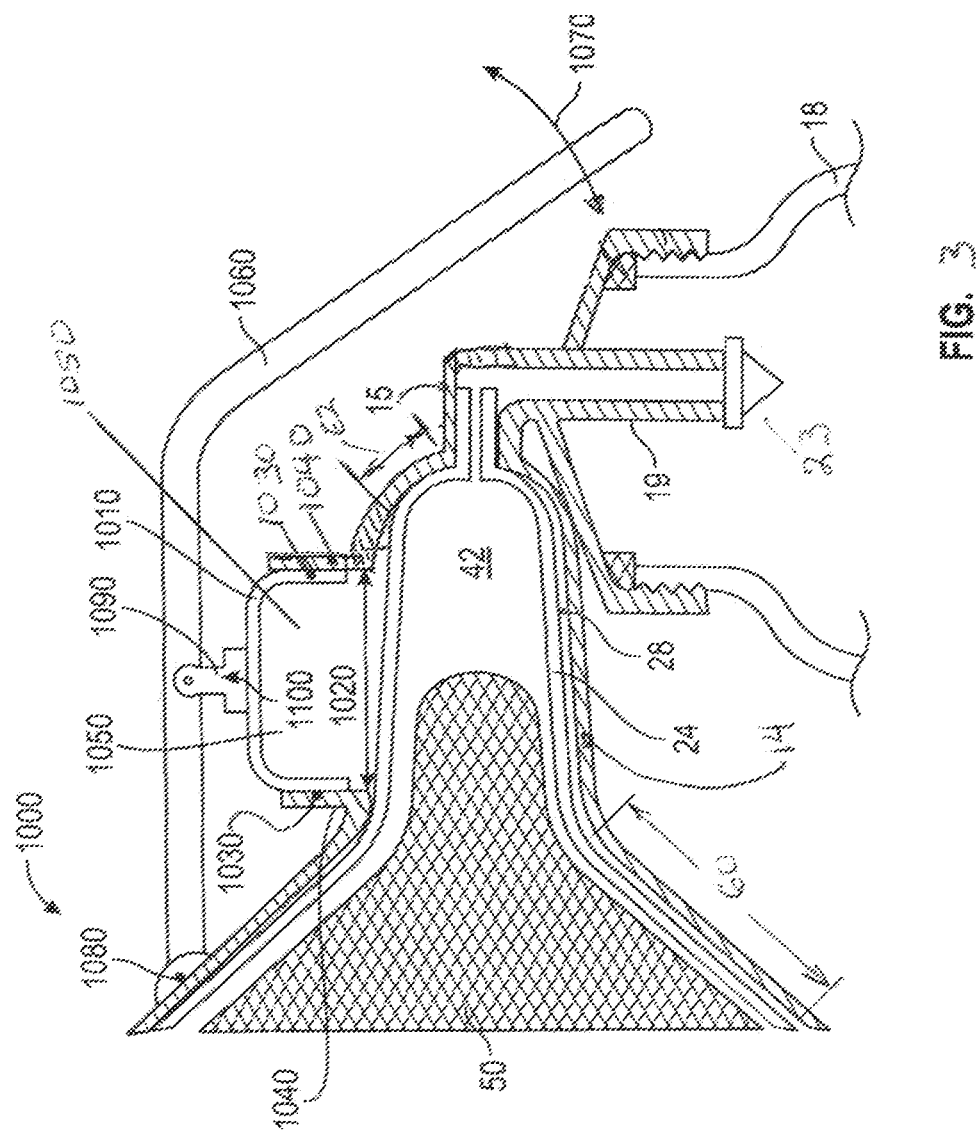
FIG. 3 shows a cross-sectional view of a breast pump in accordance with an alternate embodiment of the present invention comprising a manual pump as a variation of the design of FIG. 1A in which a functionally equivalent, mechanically actuated, diaphragm pump replaces the powered positive/negative pressure pump and electric valve system. The mechanically actuated diaphragm pump is capable of creating cyclic vacuum to extend the nipple and extract milk and of creating positive pressure to collapse an internal circumferential elastic membrane around the nipple to compress the nipple and thereby control edema. The illustrated breast pump comprises a closed system and has no media separator.

Referring to FIG. 3, a pumping head and assembled manual breast pump for extracting breast milk in accordance with an alternate embodiment of the present invention is generally designated as reference numeral 1000. This embodiment utilizes pumping head features illustrated in the embodiment of FIG. 1A. However, the valve and vacuum/pressure pump of the FIG. 1A pump are replaced by a deformable upper elastic diaphragm membrane pump. The breast pump 1100 of FIG. 3 is preferably a manually operated breast pump. In FIG. 3, where the designation numbers are the same the designation numbers in FIG. 1A, the features and functions are the same.

The membrane pump of FIG. 3 is positioned in an opening or pocket 1020 formed in the neck portion 14 of the external shell whereby the elastic diaphragm membrane 1010 is bonded at 1030 to the inside (as pictured in FIG. 3) or outside of suitably shaped extensions 1040 of the expanded neck portion or nipple tunnel section of the external shell. As illustrated in FIG. 1A, the elastic membrane 24 is bonded to the inside surface of the funnel-shaped portion 12 of the external shell along region 60 and is also sealed to the inside surface of the distal end 15 of the neck portion 14 along region 62. As so positioned, and bonded, a hermetic capsule (represented by reference numerals 1050 and 28) is formed among the deformable upper elastic diaphragm membrane 1010, the suitably shaped extensions 1040 of the expanded neck portion, the interior of the external shell 14, and the exterior of the elastic membrane 24 which is bonded to the funnel-shaped portion along regions 60 and 62.

In embodiments of the present invention, the deformable hermetic capsule 1050 described above is preferably filled with an incompressible material, such as liquid, gel or the like, but which can also be filled with gas or air.

Alternative designs of such a hermetic capsule as shown and illustrated in applicant's U.S. patent application Ser. No. 17/036,605, issued as U.S. Pat. No. 11,116,880, which is incorporated herein by reference.

In operation, once the breast and nipple 50 are inserted into the pumping head 1000, as illustrated in FIG. 3, the handle 1060 of the manual actuator is moved forward and backward by the user (as represented by arrow 1070) causing the handle 1060 to rotate around a hinge pivot 1080 and thereby moving a pushrod 1090 away from or toward the interior axial center of the neck portion of pumping head 1000. The pushrod 1090 is operatively connected, and bonded to, the top surface of the deformable upper elastic diaphragm membrane 1010. Motion of the pushrod 1090 away from the axial center of the neck portion 14 will create negative pressure within the deformable hermetic capsule 1050. This negative pressure will cause elastic membrane 24 to deform radially outward, away from the axis of the pumping head 1000 thereby creating suction around and in front of the nipple causing the nipple to extend and to extract milk.

Motion of the pushrod 1090 toward the axial center of the neck portion of pumping head 1000 will create positive pressure within the hermetic capsule. This positive pressure will cause elastic membrane 24 to deform radially inward, toward the axis of the pumping head 1000 compressing the nipple to control edema.

By controlling stroke and frequency of handle motion the user can cause the nipple to extend and retract which will repeatedly drag the areola across the inflection between the breast shield funnel portion 12 and neck portion 14 causing a mechanical stimulation of the areola. This is presumed to bring on an MER.

By controlling stroke of outward handle motion the user can increase suction in chamber 42 causing the nipple to extend and to extract breast milk. By controlling stroke of inward handle motion the user can increase pressure in chamber 42 causing compression of the nipple for control of edema. Increased pressure in chamber 42 will also cause air, or milk, to move from chamber 42 into the collection container 18 through check valve 23.

Alternate designs of the mechanical actuation means, to apply pressure to and manipulate the deformable upper elastic membrane 1010, can be used without departing from the spirit and principles of the present invention. Additional, fewer or different linkages can be used to provide the push/pull action. For example, pivot 1080 could be relocated to the distal side of the pushrod assembly 1090. This will reverse results of handle motion i.e., outward motion will create pressure in the deformable hermetic capsule 1050, inward motion will create suction. In another example, a cable could be connected to either the handle 1060 and pushrod 1090 to effectuate deformation of the capsule and thus deformation of the elastomer membrane 24 which surrounds and acts on the nipple.

Additionally, alternate positive displacement pumps to the diaphragm pump pictured in FIG. 3 are possible. For example, a piston/cylinder pump may be used without departing from the spirit and principles of the present invention.

The internal flexible membrane can deviate from the shapes pictured as 24 or 320. Alternate membranes may be preferentially thinned along their length or thinned just on proximal or distal ends. Moreover, the proximal end seal may be moved distally and/or the distal end seals may be moved proximally thereby relocating and/or shortening that portion of the internal flexible membrane which expands and contracts and thereby causing interaction with different portions of the nipple.

Breast milk from the collection container can be fed to an infant or stored for future use.

In use, the user can insert a finger into the funnel section of the breast pump head to break any residual vacuum between the breast and the funnel section.

All pumps presented in the figures above and described herein, whether powered or manual, meet all requirements of an "ideal" breast pump that mimics the mechanical and suction actions of a nursing infant, as discussed above. Notably, the present invention can (1) bring on an MER to pressurize the breast, (2) extend the nipple so milk can flow, (3) create suction of at least 180 mm Hg to extract milk and (4) apply radial (mechanical) compression to the nipple to control nipple edema.

Another embodiment of the present invention provides for self-adjustment for different diameters of nipples. To accommodate different nipple diameters, conventional pumps with hard plastic external shells and no internal elastic membranes are provided in different nipple tunnel sizes. For example, some shells come in up to 5 nipple tunnel diameters ranging between 19 mm to more than 30 mm diameter. The user must choose the appropriate nipple tunnel size based on her nipple diameter. The present invention, utilizing an elastic membrane capable of diameter expansion and contraction enables a single shield to cover a much wider range of nipple diameters. Thus, a single, or just a few different sized flanges are needed.

Although the present invention has been shown and described with respect to the detailed embodiments thereof, it will be understood by those skilled in the art that various changes in form and detail thereof may be made without departing from the spirit and scope of the invention. It is noted that the figures are to be taken as an illustrative example only and are not to scale. Additionally, it is also to be understood that the terminology used is for the purpose of describing particular embodiments only and is not intended to limit the scope of the claims of the present invention.

What is claimed is:

1. A device for extracting breast milk from a breast, said device comprising:
an external shell defining an internal cavity, said external shell including:
a neck portion defining a proximal end and a distal end; and
a feed channel defined at the distal end of the neck portion of the external shell; and
an elastic membrane disposed within the internal cavity of the external shell, said elastic membrane including:
a funnel-shaped portion configured to receive and seal against the breast of a user; and
a neck portion extending from the funnel-shaped portion and defining a proximal end and a distal end adapted to receive and position a nipple of the breast, said neck portion of the elastic membrane narrowing at said distal end of the neck portion of the elastic membrane to an exit port of the elastic membrane, wherein said neck portion of the elastic membrane fits in the neck portion of the external shell such that the exit port of the elastic membrane is in operative communication with the feed channel, and
wherein further, when the nipple of the user is positioned in the neck portion of the elastic membrane, said neck portion of the elastic membrane defines an unoccupied volume between a nipple tip and the distal end of said neck portion of the elastic membrane;

wherein the unoccupied volume between the nipple tip and the distal end of said elastic membrane is in operative communication, via the exit port, with a suction source; and wherein the exterior of the elastic membrane is sealed to the interior of the external shell to form a hermetic chamber between the neck portion of the external shell and the neck portion of the elastic membrane, wherein the external shell further comprises a side port configured to operatively connect the hermetic chamber to the suction source and the positive pressure source;

wherein the suction source is configured to control pressure in the hermetic chamber via the side port;

wherein the suction source is configured to control pressure in the unoccupied volume via the exit port of the elastic membrane;

wherein the elastic membrane is configured to receive a suction pressure below atmospheric pressure from the suction source via the distal end of the neck portion of the elastic membrane that is applied to the unoccupied volume inside the elastic membrane around and in front of the nipple positioned therein to extend the nipple towards the distal end of the neck portion of said elastic membrane and to extract breast milk, wherein, the neck portion of the elastic membrane is configured to relax radially outwardly, allowing clearance for the nipple to extend when the suction pressure is introduced into the hermetic chamber via the side port, wherein said suction pressure in the hermetic chamber is equivalent to the suction pressure applied to the unoccupied volume inside the elastic membrane around and in front of the nipple positioned therein, and wherein a portion of the elastic membrane of the hermetic chamber is configured to expand radially inwardly when a positive pressure greater than the suction pressure then present within the unoccupied volume inside the elastic membrane around and in front of the nipple positioned therein is introduced into the hermetic chamber from the positive pressure source via the side port causing the elastic membrane as so expanded to contact and compress the nipple to control nipple edema;

wherein the neck portion of the elastic membrane is configured for both radial outward and radially inward movement with alternating application of the suction pressure and the positive pressure into the hermetic chamber via the side port.

2. The device according to claim 1, wherein the feed channel leads into a collection container to receive extracted breast milk.

3. The device according to claim 2, further comprising an attachment portion comprising threads for connecting the device to the collection container.

4. The device according to claim 3, wherein the suction device is connected to the device through the attachment portion, whereby said suction device is configured to apply a constant suction to evacuate an interior portion inside the elastic membrane around and in front of the nipple positioned therein, and the collection container.

5. The device according to claim 4, further comprising a seal positioned between the attachment portion and the collection container when connected to one another.

6. The device according to claim 1, wherein the suction source or the positive pressure source can be connected to the device via at least one opening in the external shell.

7. The device according to claim 6, further comprising tubing and an electric valve assembly connecting the suction source both to the inside the elastic membrane around and in front of the nipple positioned and via the at least one opening in the external shell to the hermetic chamber or the electric valve assembly can connect the positive pressure source via the at least one opening in the external shell only to the hermetic chamber.

8. The device according to claim 1, wherein the elastic membrane includes a distally facing ring-shaped groove into which the proximal end of the neck portion of the external shell fits.

9. The device according to claim 7, wherein the suction source comprises a source capable of cyclic suction that is connected to the device through the feed channel, and further comprising a check valve fitted between the feed channel and the collection container to prevent fluid flow from the collection container into the feed channel and further containing a hole through the attachment portion to keep the collection container at atmospheric pressure.

10. The device according to claim 1, wherein the suction pressure and the positive pressure are both supplied by a single pump.

11. A device for extracting breast milk from a breast, said device comprising:
an external shell defining an internal cavity, said external shell including:
a neck portion defining a proximal end and a distal end; and
a feed channel defined at the distal end of the neck portion of the external shell; and
an elastic membrane disposed within the internal cavity of the external shell, said elastic membrane including:
a funnel-shaped portion configured to receive and seal against the breast of a user; and
a neck portion extending from the funnel-shaped portion and defining a proximal end and a distal end adapted to receive and position a nipple of the breast, said neck portion of the elastic membrane narrowing at said distal end of the neck portion of the elastic membrane to an exit port of the elastic membrane, wherein said neck portion of the elastic membrane fits in the neck portion of the external shell such that the exit port of the elastic membrane is in operative communication with the feed channel, and wherein further, when the nipple of the user is positioned in the neck portion of the elastic membrane, said neck portion of the elastic membrane defines an unoccupied volume between a nipple tip and the distal end of said neck portion of the elastic membrane;

wherein the unoccupied volume between the nipple tip and the distal end of said elastic membrane is in operative communication, via the exit port, with a source of at least one of positive pressure, atmospheric pressure and/or negative pressure; and wherein the exterior of the elastic membrane is sealed to the interior of the external shell at proximal and distal ends of the neck portion of the external shell and of the elastic membrane so to form a hermetic chamber between the neck portion of the external shell and the neck portion of the elastic membrane;

wherein the source of at least one of positive pressure, atmospheric pressure and/or negative pressure is operative to control pressure in the hermetic chamber via a side port of the external shell;

wherein the source of at least one of positive pressure, atmospheric pressure and/or negative pressure is operative to control pressure in the unoccupied volume via the exit port of the elastic membrane;

wherein the elastic membrane is configured to receive, through the distal end of the neck portion of the elastic membrane, a suction pressure below atmospheric pressure that is applied to the unoccupied volume inside the elastic membrane around and in front of the nipple positioned therein to extend the nipple towards the distal end of the neck portion of said elastic membrane and to extract breast milk;

wherein the hermetic chamber is in operative communication with the source of at least one of positive pressure, atmospheric pressure and/or negative pressure via the side port, wherein a portion of the elastic membrane of the hermetic chamber is configured to deform radially outwardly, allowing clearance for the nipple to extend when a suction pressure is introduced within the hermetic chamber via the side port, wherein said suction pressure in the hermetic chamber is equivalent to the suction pressure then present within the unoccupied volume inside the elastic membrane around and in front of the nipple positioned therein, wherein the portion of the elastic membrane of the hermetic chamber is configured to expand radially inwardly when a pressure greater than the suction pressure then present within the unoccupied volume inside the elastic membrane around and in front of the nipple positioned therein is introduced via the at least one opening into the hermetic chamber to compress the nipple to control nipple edema.

12. The device according to claim 11, wherein the hermetic chamber is filled with one of a liquid or a gas.

13. The device according to claim 11, wherein the source of at least one of positive pressure, atmospheric pressure and/or negative pressure is a source of alternating positive and negative pressure and comprises an electrically driven positive displacement pump.

14. The device according to claim 11, wherein the source of at least one of positive pressure, atmospheric pressure and/or negative pressure is a source of alternating positive and negative pressure and comprises a manually operated actuating mechanism.

15. The device according to claim 14, wherein the manually-operated actuating mechanism comprises a handle and pushrod assembly which mechanically deforms an elastic membrane set in a portion of the external shell, such deformation increasing or decreasing volume of and thus pressure within the hermetic chamber; increased pressure causing the elastic membrane to deform towards the axis of the neck portion of the elastic membrane; decreased pressure causing the elastic membrane to deform away from the axis of the neck portion of the elastic membrane.

16. The device according to claim 11, wherein the suction introduced inside the elastic membrane around and in front of the nipple positioned therein is cyclic.

17. A method for extracting breast milk from a breast using a breast pump, said method comprising:
providing a breast pump comprising:
an external shell defining an internal cavity, said external shell including:
a neck portion defining a proximal end and a distal end; and
a feed channel defined at the distal end of the neck portion of the external shell; and
an elastic membrane disposed within the internal cavity of the external shell, said elastic membrane including:
a funnel-shaped portion configured to receive and seal against the breast of a user;
a neck portion extending from the funnel-shaped portion and defining a proximal end and a distal end adapted to receive and position a nipple of the breast, said neck portion of the elastic membrane narrowing at said distal end of the neck portion of the elastic membrane to an exit port of the elastic membrane, wherein said neck portion of the elastic membrane fits in the neck portion of the external shell such that the exit port of the elastic membrane is in operative communication with the feed channel, wherein the external shell further comprises a side port configured to operatively connect the hermetic chamber to a suction source and a positive pressure source;
wherein, when the nipple of the user is positioned in the neck portion of the elastic membrane, said neck portion of the elastic membrane defines an unoccupied volume between a nipple tip and the distal end of said elastic membrane;
wherein the unoccupied volume between the nipple tip and the distal end of said elastic membrane is in operative communication, via the exit port, with the suction source; and
wherein the exterior of the elastic membrane is sealed to the interior of the external shell at proximal and distal ends of the neck portion of the external shell and of the elastic membrane so to form a hermetic chamber between the neck portion of the external shell and the neck portion of the elastic membrane;
wherein the suction source and the positive pressure source are operative to control pressure in the hermetic chamber via a side port of the external shell;
wherein the suction source and the positive pressure source are operative to control pressure in the unoccupied volume via the exit port of the elastic membrane;
applying, via the distal end of the neck portion of the elastic membrane, suction below atmospheric pressure to the unoccupied volume inside the elastic membrane around and in front of the nipple positioned therein, to extend the nipple towards the distal end of the neck portion of said elastic membrane and to extract breast milk;
introducing, via the side port of the external shell, a suction pressure inside the hermetic chamber which is equivalent to the suction pressure then present within the unoccupied volume inside the elastic membrane to cause the neck portion of the elastic membrane to relax radially outwardly, allowing clearance for the nipple to extend; and
introducing, via the side port, a positive or atmospheric pressure greater than the suction pressure then present within the unoccupied volume inside the elastic membrane around and in front of the nipple positioned therein into the hermetic chamber so as to expand the neck portion of the elastic membrane radially inwardly, thereby causing the elastic membrane to compress the nipple to control nipple edema.

18. The method of extracting breast milk according to claim 17, wherein the internal cavity of the external shell is in operative communication with a suction source connected to the breast pump, said suction source being used to apply the suction below atmospheric pressure inside the elastic membrane around and in front of the nipple positioned therein, and also to introduce suction inside the hermetic chamber allowing the neck portion of the elastic membrane to relax it radially outwardly.

19. The method of extracting breast milk according to claim 17, wherein the internal cavity of the external shell is in operative communication with a positive pressure source connected to the breast pump via the at least one opening in the external shell, said positive pressure source being used to introduce a pressure greater than the suction then present inside the elastic membrane around and in front of the nipple positioned therein into the hermetic chamber to expand the neck portion of the elastic membrane radially inwardly to compress the nipple and control nipple edema.

20. The method of extracting breast milk according to claim 19, wherein the suction below atmospheric pressure applied inside the elastic membrane around and in front of the nipple positioned therein is cyclic.

\* \* \* \* \*